(12) United States Patent
Tsai et al.

(10) Patent No.: US 12,188,865 B2
(45) Date of Patent: Jan. 7, 2025

(54) OPTICAL MACHINE OF SMOKE DETECTOR

(71) Applicant: PIXART IMAGING INC., Hsin-Chu County (TW)

(72) Inventors: Cheng-Nan Tsai, Hsin-Chu County (TW); Yen-Chang Chu, Hsin-Chu County (TW); Chih-Ming Sun, Hsin-Chu County (TW); Chi-Chih Shen, Hsin-Chu County (TW); Kuo-Hsiung Li, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 32 days.

(21) Appl. No.: 17/722,132

(22) Filed: Apr. 15, 2022

(65) Prior Publication Data

US 2023/0060584 A1 Mar. 2, 2023

Related U.S. Application Data

(60) Provisional application No. 63/237,153, filed on Aug. 26, 2021.

(51) Int. Cl.
| | | |
|---|---|---|
| *G01N 21/47* | (2006.01) | |
| *G01N 33/00* | (2006.01) | |
| *G08B 17/107* | (2006.01) | |
| *G01N 21/53* | (2006.01) | |

(52) U.S. Cl.
CPC ..... *G01N 21/4738* (2013.01); *G01N 33/0027* (2013.01); *G08B 17/107* (2013.01); *G01N 21/53* (2013.01); *G01N 2291/0217* (2013.01)

(58) Field of Classification Search
CPC .......... G01N 21/4738; G01N 33/0027; G01N 21/53; G01N 2291/0217; G08B 17/107; G08B 29/18

See application file for complete search history.

(56) References Cited

U.S. PATENT DOCUMENTS

| | | | |
|---|---|---|---|
| 11,322,666 B2* | 5/2022 | Coffy | G01S 7/4813 |
| 2015/0379846 A1* | 12/2015 | Bressanutti | G08B 17/107 |
| | | | 340/630 |
| 2020/0103613 A1* | 4/2020 | Shen | H01L 27/14618 |
| 2020/0312897 A1* | 10/2020 | Hsieh | H01L 27/14683 |
| 2020/0363312 A1 | 11/2020 | Deliwala | |
| 2022/0140173 A1* | 5/2022 | Shen | H01L 31/0203 |
| | | | 257/84 |

FOREIGN PATENT DOCUMENTS

| | | | |
|---|---|---|---|
| CN | 103177523 A | 6/2013 | |
| JP | 3476326 B2 * | 12/2003 | ... H01L 2224/48091 |
| JP | 2007059657 A * | 3/2007 | |

* cited by examiner

*Primary Examiner* — Michelle M Iacoletti
*Assistant Examiner* — Judy Dao Tran
(74) *Attorney, Agent, or Firm* — HAUPTMAN HAM, LLP

(57) ABSTRACT

There is provided an optical machine of a smoke detector including a substrate, a light source, a light sensor and a light blocking member. The light source and the light sensor are arranged on the substrate in a first direction. The light blocking member is arranged upon the light source and blocks a part of an emission angle of the light source in the first direction far away from the light sensor.

12 Claims, 8 Drawing Sheets

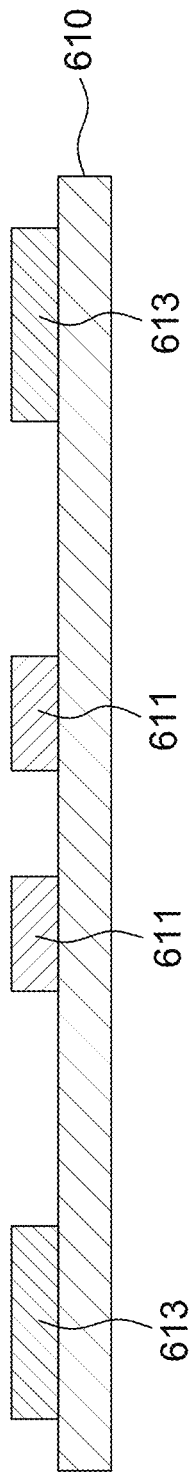
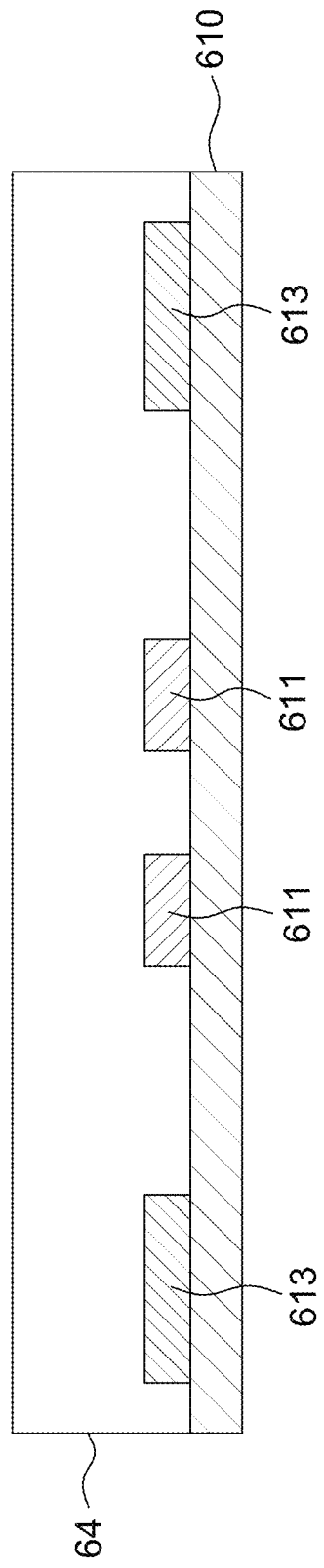

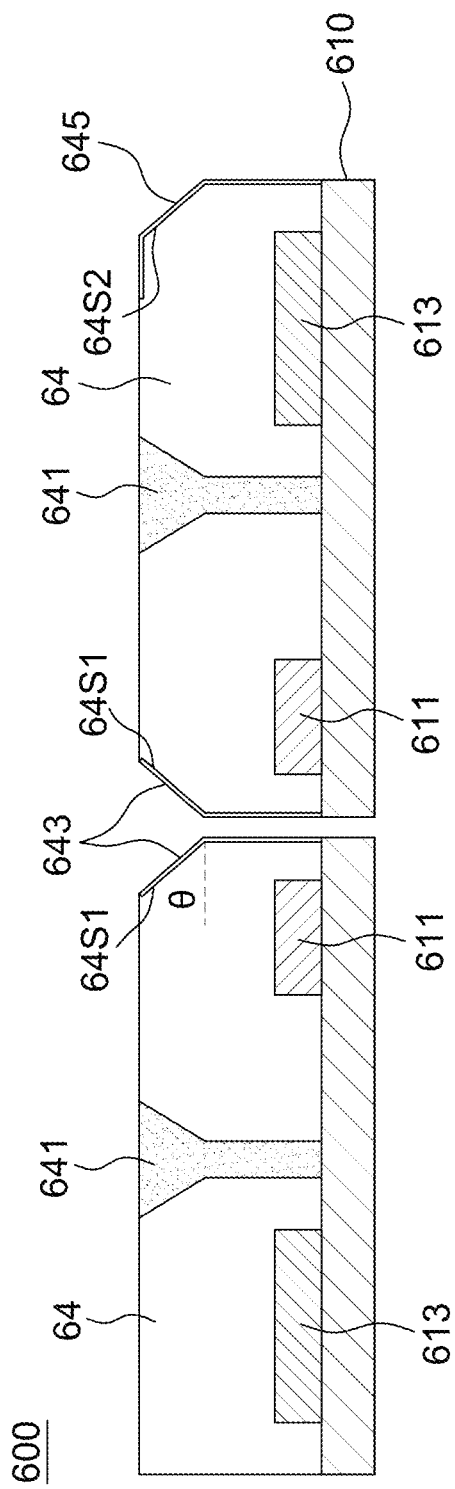
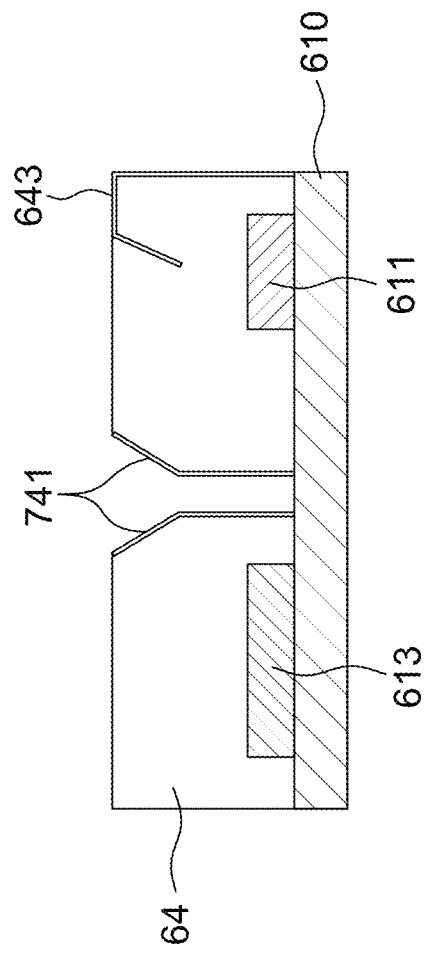
FIG. 6E
FIG. 7

000
OPTICAL MACHINE OF SMOKE DETECTOR

RELATED APPLICATIONS

The present application claims the priority benefit of U.S. Provisional Application Ser. No. 63/237,153, filed on Aug. 26, 2021, the disclosure of which is hereby incorporated by reference herein in its entirety.

BACKGROUND

1. Field of the Disclosure

This disclosure generally relates to an optomechanical structure and, more particularly, to a smoke detector and a miniaturized optical machine that reduce a false alarm rate of the smoke detector caused by environmental change by decreasing detected reference light intensity of a light sensor.

2. Description of the Related Art

It is known that circuit features of an optoelectronic component can change with environmental change. For example, if smoke detectors are arranged outdoors, the false alarm can occur due to the environmental change.

For example referring to FIG. 1, it is a schematic diagram of a false alarm caused by a brightness variation detected by a light sensor of an optical smoke detector with temperature variation. Generally speaking, the optical smoke detector is set to give an alarm when detected brightness exceeds an alarm level. For example, when smoke enters a detection space of the smoke detector, the detected brightness (shown as smoke profile) exceeds the alarm level.

When the environmental temperature maintains constant, e.g., at 25° C., the detected brightness of the light sensor is substantially fixed if no smoke enters the detection space. However, with the decreasing of environmental temperature, e.g., to 15° C., emission intensity of a light source is changed to accordingly cause the detected brightness of the light sensor to exceed the alarm level even if no smoke entering the detection space such that a false alarm is triggered.

Accordingly, the present disclosure provides an optical machine of a smoke detector with a low false alarm rate and a small size.

SUMMARY

The present disclosure provides an optical machine of a smoke detector that can reduce detected reference light intensity of a light sensor thereof so as to reduce a false alarm rate of the smoke detector caused by an environmental change and to have higher sensitivity.

The present disclosure further provides a miniaturized optical machine so as to make it possible to reduce a total size of a smoke detector.

The present disclosure provides an optical machine of a smoke detector including a substrate, a light sensor, a first light source and a light blocking member. The light sensor is arranged on the substrate. The first light source is arranged on the substrate and having a first emission angle. The light blocking member includes a first opening upon the first light source, and the first opening exposes a part of the first emission angle of the first light source close to the light sensor.

The present disclosure further provides an optical machine of a smoke detector including a substrate, a light sensor, a light source, a transparent gel and a first light blocking layer. The light sensor is arranged on the substrate. The light source is arranged on the substrate and having an emission angle. The transparent gel encapsulates the light sensor and the light source, and has a first tilted surface extending from a first side of the transparent gel close to the light source to above the first light source. The first light blocking layer is formed on the first side and the first tilted surface of the transparent gel to block a part of the emission angle of the light source far away from the light sensor.

The present disclosure further provides an optical machine of a smoke detector including a substrate, a light sensor, a transparent gel and a light blocking layer. The light sensor is arranged on the substrate. The transparent gel encapsulates the light sensor, and has a tilted surface extending from a side of the transparent gel to above the light sensor. The light blocking layer is formed on the side and the tilted surface of the transparent gel to block a part of an above region of the light sensor.

BRIEF DESCRIPTION OF THE DRAWINGS

Other objects, advantages, and novel features of the present disclosure will become more apparent from the following detailed description when taken in conjunction with the accompanying drawings.

FIGS. 6A to 6E are cross sectional views of manufacturing an optical machine of a smoke detector according to a second embodiment of the present disclosure.

FIG. 7 is another cross sectional view of an optical machine of a smoke detector according to a second embodiment of the present disclosure.

DETAILED DESCRIPTION OF THE EMBODIMENT

It should be noted that, wherever possible, the same reference numbers will be used throughout the drawings to refer to the same or like parts.

One objective of the present disclosure is to provide a smoke detector that increases a variation ratio of light intensity caused by smoke entering the smoke detector by reducing reference light intensity to accordingly improve detection sensitivity and reduce a false alarm rate. The present disclosure further provides a miniaturized optical machine and a manufacturing method thereof.

Figure 1:
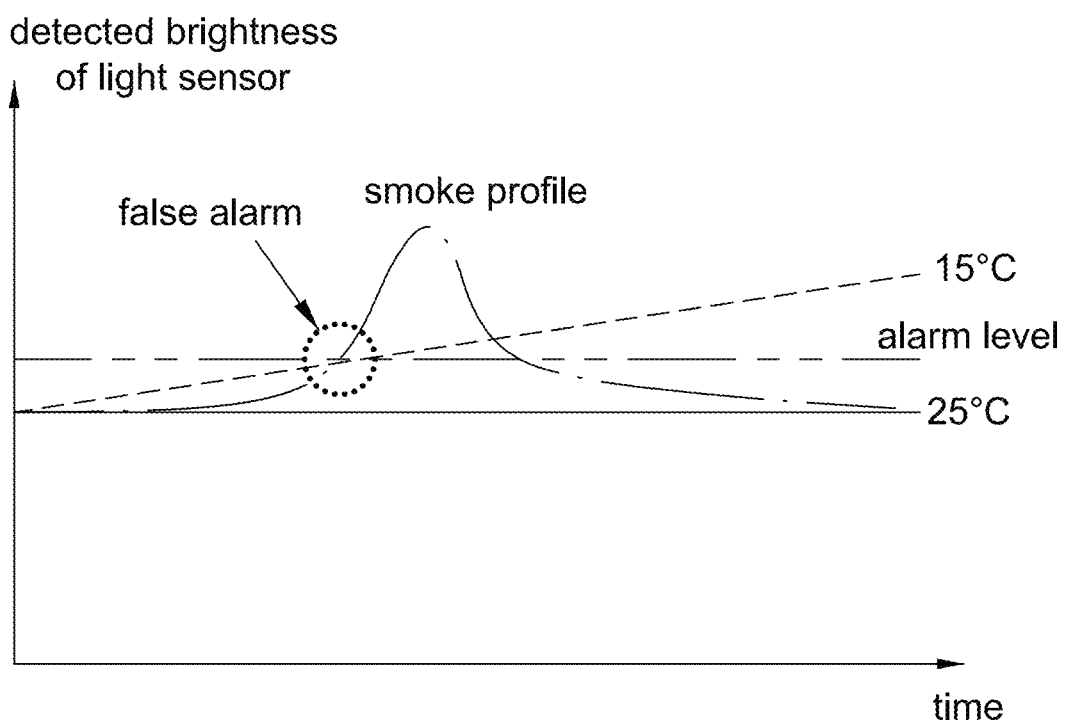
FIG. 1 is a schematic diagram of a false alarm of a smoke detector caused by a variation of detected brightness with temperature.
Figure 2A:
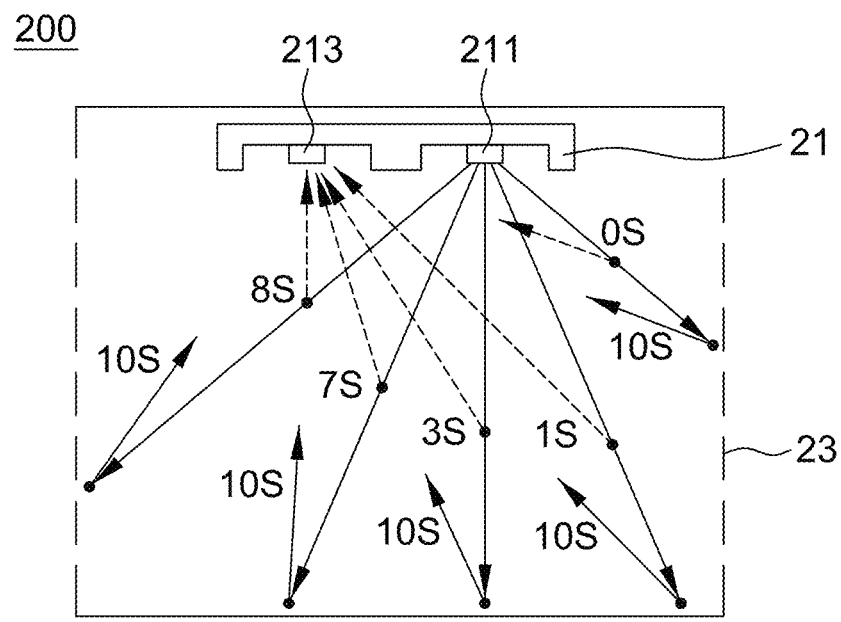
FIGS. 2A and 2B are schematic diagrams of light propagation in a smoke detector according to some embodiments of the present disclosure.
Figure 2B:
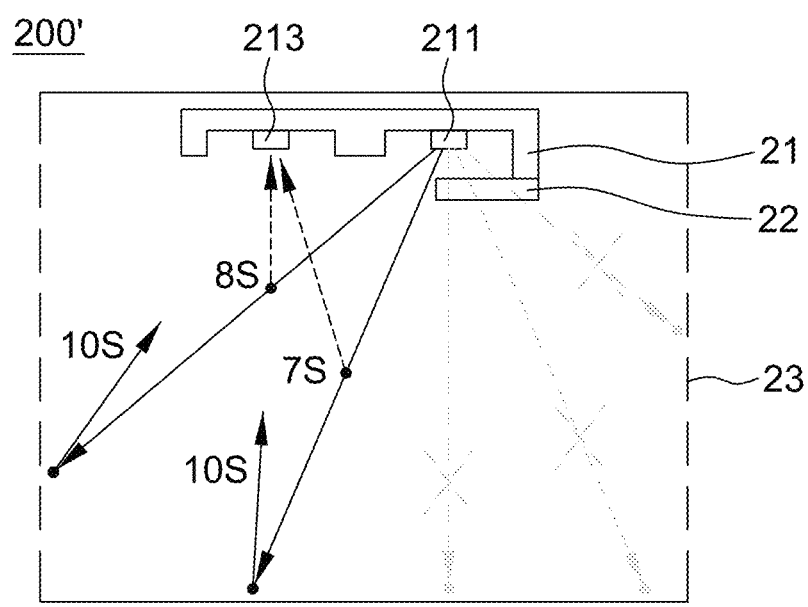

Please refer to FIGS. 2A and 2B, they are schematic diagrams of light propagation in a smoke detector 200 according to some embodiments of the present disclosure. FIG. 2A shows that the smoke detector 200 includes an optical machine 21 and a cover 23, wherein the cover 23 has a suitable structure without particular limitations as long as the cover 23 blocks ambient light to enter the cover 23 but allows air to go into an inner space thereof.

A light source 211 of the optical machine 21 emits light to illuminate an inner surface of the cover 23 and particles (e.g., smoke) therein. It is assumed that each spot of the inner surface has identical reflection light intensity 10S (which is detected by a light sensor 213), and particles at different locations have different reflection light intensity, e.g., shown as 0 S, 1 S, 3 S, 7 S and 8 S, but not limited thereto. In this case, a total reflection light intensity of particles is 19 S, and a total reflection light intensity from the inner surface is 50 S (i.e. reference light intensity herein), and thus a ratio therebetween is 0.38. FIG. 2B shows that the smoke detector 200 is further arranged with a light blocking member 22 which blocks a part of emission angle of the light source 21 such that only a part of emission angle generates reflection light. In this case, a total reflection light intensity of particles is 15 S, and a total reflection light intensity from the inner surface is 20 S, and thus a ratio therebetween is 0.75. That is, by arranging the light blocking member 22, the ratio between the reflection light intensity of smoke with respect to the reference light intensity is significantly increased, to accordingly improve detection sensitivity of the smoke detector.

Figure 3:
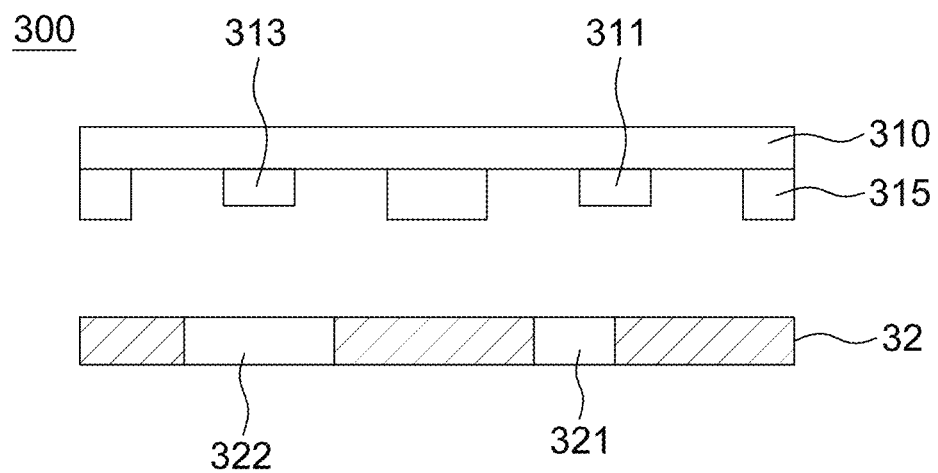
FIG. 3 is a cross sectional view of an optical machine of a smoke detector according to a first embodiment of the present disclosure.
Figure 4A:
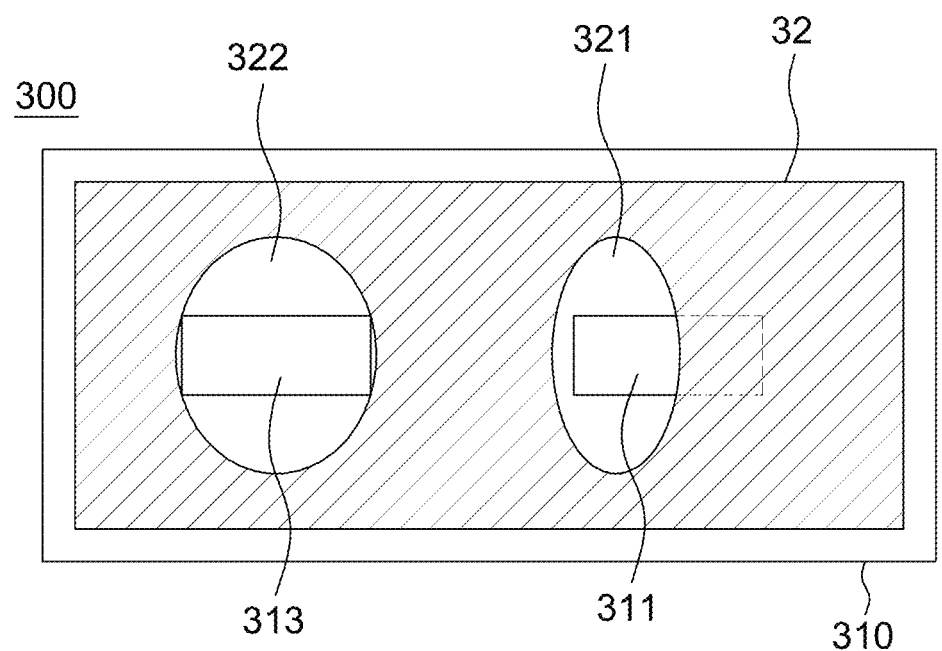
FIG. 4A is a top view of an optical machine of a smoke detector according to a first embodiment of the present disclosure.

Please refer to FIGS. 3 and 4A, FIG. 3 is a cross sectional view of an optical machine 300 of a smoke detector according to a first embodiment of the present disclosure; and FIG. 4A is a top view of an optical machine 300 of a smoke detector according to a first embodiment of the present disclosure. As shown in FIGS. 2A and 2B, the optical machine 300 is arranged inside a cover of the smoke detector for detecting reference light intensity at normal time and detecting increment of detected light intensity with existence of smoke.

The optical machine 300 includes a substrate 310, a first light source 311, a light sensor 313 and a light blocking member 32. In one aspect, the optical structure 300 further includes a side wall 315 arranged on the substrate 310 and surrounding the light sensor 313 and the first light source 311. The light blocking member 32 is preferably attached to a top surface of the side wall 315 such that the first light source 311 and the light sensor 313 are located inside inner spaces formed by the substrate 310, the side wall 315 and the light blocking member 32. Preferably, the inner space in which the light source 311 is located and the inner space in which the light sensor 313 is located are separated by the side wall 315 such that light emitted by the light source 311 is not directly (i.e. without reflection) received by the light sensor 313.

The substrate 31 is a printed circuit board or a flexible board without particular limitations as long as the substrate 31 is electrically coupled with the first light source 311 and the light sensor 313, and transmits electric signals and power required thereby.

The light sensor 313 is a CMOS image sensor or a single photon avalanche diode (SPAD). The light sensor 313 is arranged on the substrate 310, such as via wire bonding, but not limited to. In other aspects, the light sensor 313 is electrically coupled and fixed on the substrate 310 using other known ways.

Figure 5:
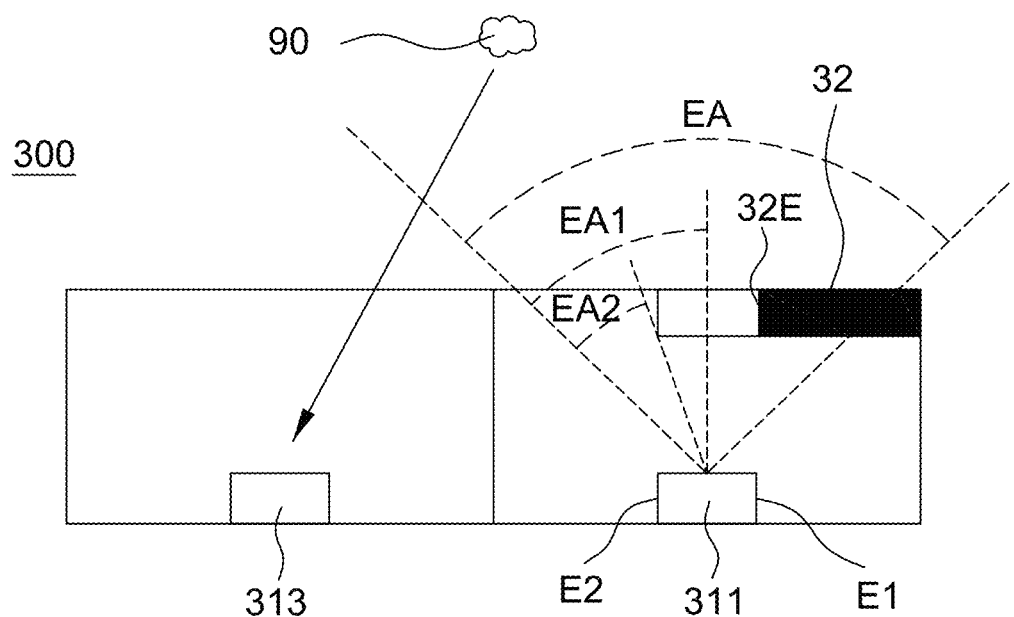
FIG. 5 is an operational schematic diagram of an optical machine of a smoke detector according to a first embodiment of the present disclosure.

The first light source 311 is a light emitting diode or a laser diode, and has a first emission angle EA, e.g., referring to FIG. 5. The first light source 311 is arranged on the substrate 310 such as via wire bonding, but not limited to. In other aspects, the first light source 311 is electrically coupled and fixed on the substrate 310 using other known ways. FIG. 4A shows that the first light source 311 and the light sensor 313 are arranged on the substrate 310 in a first direction (shown as left-right direction).

It should be mentioned that the first light source 311 and the light sensor 313 are not limited to be arranged parallel to upper and lower edges of the substrate 310.

The light blocking member 32 is made of opaque materials such as plastic, rubber, wood, metal or a combination thereof without particular limitations. The light blocking member 32 has a first opening 321 upon the first light source 311, and blocks a part of (shown as right part) of a first emission angle EA of the first light source 311 far away from the light sensor 313, i.e. the first opening 321 exposing a part of (shown as left part) the first emission angle EA of the first light source 311 close to the light sensor 313. In this way, a part of emission light of the first light source 311 is blocked as shown in FIG. 2B to reduce detected reference light intensity of the light sensor 313.

The light blocking member 32 further has a second opening 322 upon the light sensor 313. In one aspect, the second opening 322 exposes the whole light sensor 313. In another aspect, the light blocking member 32 blocks a part of (shown as left part) of the light sensor 313 far away from the first light source 311, i.e. the second opening 322 exposing a part of (shown as right part) the light sensor 313 close to the first light source 311, so as to further reduce the detected reference light intensity of the light sensor 313.

Please refer to FIG. 5 again, it shows that when the light blocking member 32 blocks different areas of the first light source 311, reflection light intensity of the smoke 90 is changed. In one aspect, an opening edge 32E of the first opening 321 far away from the light sensor 313 is aligned with a first edge E1 of the first light source 311 far away from the light sensor 313. It is seen from FIG. 5 that a part of the first emission angle EA of the first light source 311 is blocked by the light blocking member 32. In another aspect, the opening edge 32E of the first opening 321 far away from the light sensor 313 is aligned with a central line of the first light source 311, and an effective emission angle changes to EA1. In an alternative aspect, the opening edge 32E of the first opening 321 far away from the light sensor 313 is aligned with a second edge E2 of the first light source 311 close to the light sensor 313, and an effective emission angle changes to EA2.

In an alternative aspect, the opening edge 32E of the first opening 321 far away from the light sensor 313 is arranged between a first edge E1 of the first light source 311 and a central line of the first light source 311. The opening edge 32E is closer to the first edge E1 and farther from the central line, e.g., the light blocking member 32 blocking less than 25% of the first light source 311. The purpose of arranging the first opening 321 in this way is to keep enough reference light intensity when there is no smoke in the cover, e.g., the cover 23 shown in FIGS. 2A and 2B. If the reference light intensity is too weak, scattered light intensity (i.e. reflected by smoke 90) can fluctuate significantly in different operating conditions.

In the present disclosure, an area of the first light source 311 to be blocked by the light blocking member 32 is previously determined by parameters including, for example, light emission intensity, arranged environment of the smoke detector, reflectivity of an inner surface of the smoke detector and required sensitivity.

Figure 4B:
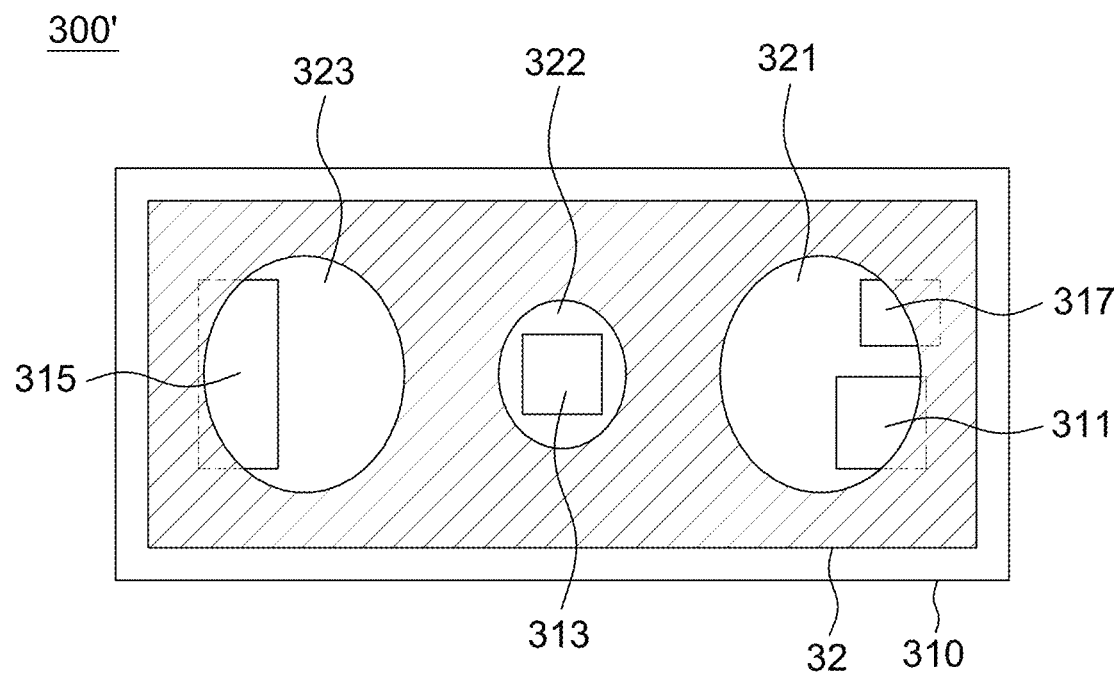
FIG. 4B is another top view of an optical machine of a smoke detector according to a first embodiment of the present disclosure.

Please refer to FIG. 4B, it is another top view of an optical machine 300' of a smoke detector according to a first embodiment of the present disclosure. In this aspect, the optical machine 300' further includes a second light source 315 having a second emission angle (also referring to FIG. 5). FIG. 4B shows that the first light source 311, the light sensor 322 and the second light source 315 are arranged on the substrate 310 along the first direction, and the light sensor 322 is between the first light source 311 and the second light source 315. Preferably, the first light source 311 and the second light source 315 emit light of different wavelengths. For example, emission light of the first light source 311 has a wavelength of 460 nm, and emission light of the second light source 315 has a wavelength of 880 nm, but not limited thereto. One objective of arranging light sources of different wavelengths at two opposite sides of the light sensor is referred to U.S. patent application Ser. No. 17/320,222, entitled "smoke detector" filed on May 14, 2021, and assigned to the same assignee of the present application, and the full disclosure of which is incorporated herein by reference.

In this aspect, the light blocking member 32 further has a third opening 323 upon the second light source 315, and light blocking member 32 blocks a part of (shown as left part) a second emission angle of the second light source 315 far away from the light sensor 313, i.e. the third opening 323 exposing a part of (shown as right part) the second emission angle of the second light source 315 close to the light sensor 313. In this aspect, the second opening 322 preferably exposes the whole light sensor 322. In other aspects, the optical machine 300' is further arranged with a third light source 317, which emits a light wavelength, e.g., 525 nm, different from the first light source 311 and the second light source 315, but the present disclosure is not limited to.

It should be mentioned that although FIG. 4B shows that the third light source 317 and the first light source 311 are at the same side of the light source 313, the present disclosure is not limited thereto. In other aspects, the third light source 317 is located at the same side of the light sensor 313 with the second light source 315, i.e. left side.

It should be mentioned that although FIG. 4B shows that the third light source 317 and the first light source 311 shares the first opening 321, the present disclosure is not limited thereto. In other aspects, the light blocking member 32 further has an individual opening corresponding to the third light source 317 and separated from the first opening 321, i.e. each light source corresponding to a respective opening. In the present disclosure, the light blocking member 32 covers a part of an emission angle, referring to FIG. 5, of every light source.

The smoke detect 300 has a larger size when a light blocking member 32 is used to be attached to the side wall 315. The present disclosure further provides an optical machine that can reduce a total size of the smoke detector.

Please refer to FIG. 6E, it is a cross sectional view of an optical machine 600 of a smoke detector according to a second embodiment of the present disclosure. The optical machine 600 also includes a substrate 610, a light source 611 and a light sensor 613, which are respectively identical to the above substrate 310, light source 311 and light sensor 313, and thus details thereof are not repeated herein. The difference between the second embodiment and the first embodiment is that the optical machine 600 does not use a light blocking member to cover upon the optical machine 600 so as to reduce the size.

The optical machine 600 has a transparent gel 64 for encapsulating the light sensor 613, the light source 611 and a part of surface of the substrate 610, and has a first tilted surface 64S1 extending from a first side of the transparent gel 64 close to the light source 611 to above the light source 611. An angle (with respect to a surface of the substrate 610) of the first tilted surface 64S1 is between 15 degrees and 80 degrees, but not limited thereto. The transparent gel 64 is made of any suitable transparent material (especially transparent to emission light of the light source 611) without particular limitations, and maintains solid state under room temperature.

The optical machine 600 further has a first light blocking layer 643 formed on the first side and the first tilted surface 64S1 of the transparent gel 64 so as to block a part of an emission angle of the light source 300 far away from the light sensor 613. In this embodiment, the first light blocking layer 643 is a metal layer formed on the surface of the transparent gel 64 by, for example, sputtering, evaporation or coating. The metal is light reflective material or light absorption material. The light reflective material is selected from Al, Ag and Au, but not limited to. The light absorption material is selected from Cr, but not limited to. The thickness of the metal layer is, for example, between 0.5 μm and 10 μm.

Depending on how much the light source 611 is desired to be blocked (referring to FIG. 5), an angle and a length of the first tilted surface 64S1 is determined. Furthermore, depending on how much the light source 611 is desired to be blocked, it is able to determine whether to extend the first light blocking layer 643 to an upper surface of the transparent gel 64. For example, if it is desired to form the effective emission angle EA2, the first light blocking layer 64 is extended from the first tilted surface 64S1 to cover a part of an upper surface of the transparent gel 64 above the light source 611.

To prevent emission light of the light source 611 from directly propagating to the light sensor 613, the optical machine 600 further includes a light blocking wall 641 in the transparent gel 64, and between the light source 611 and the light sensor 613. The light blocking wall 641 is formed by filling opaque material inside a vertical trench of the transparent gel 64, wherein the material of the light blocking wall 641 is not particularly limited as long as the emission light of the light source 611 is blocked. In one aspect, a width at an upper part of the light blocking wall 641 is larger than that at a lower part of the light blocking wall 641 to improve the light blocking effect.

To further reduce detected reference light intensity of the light sensor 613, the optical machine 600 further includes a second light blocking layer 645 formed on a second side of the transparent gel 64 close to the light sensor 613 and on a part of the upper surface of the transparent gel 64 upon the light sensor 613. For example, the transparent gel 64 further has a second tilted surface 64S2 extending from the second side to above the light sensor 613, and the second light blocking sensor 645 is formed on the second tilted surface 64S2. An angle (with respect to the surface of substrate 610) of the second tilted surface 64S2 is between 15 degrees and 80 degrees, which is identical to or different from that of the first tilted surface 64S1 without particular limitations.

It should be mentioned that although the above embodiments are illustrated in the way that the light blocking layer is formed on the first side and the second side of the transparent gel 64, the present disclosure is not limited thereto. In other aspects, the light blocking layer is formed at all side surfaces of the transparent gel 64.

Figure 6C:
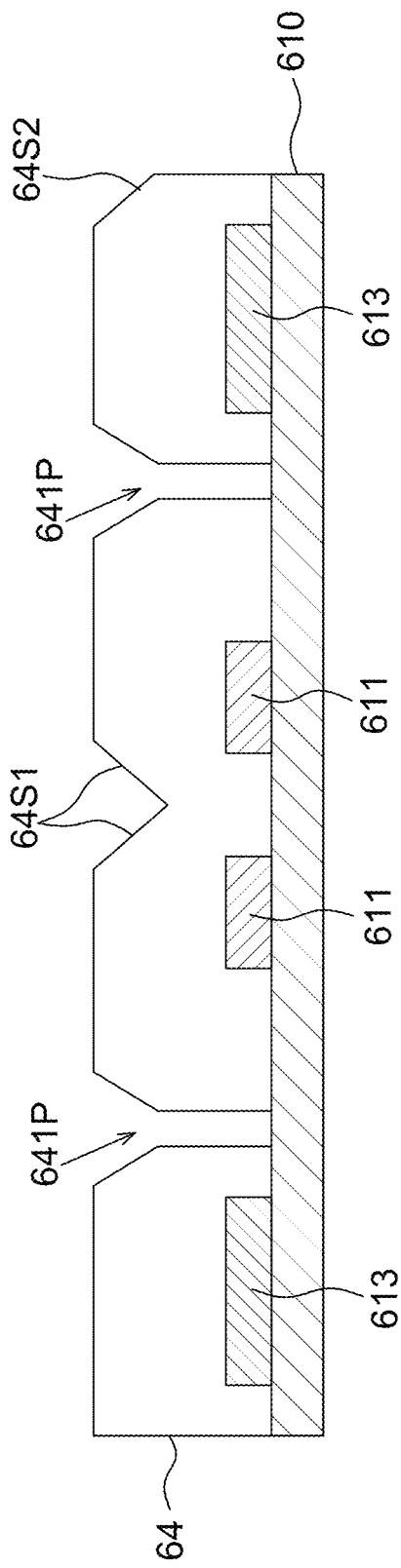
Figure 6D:
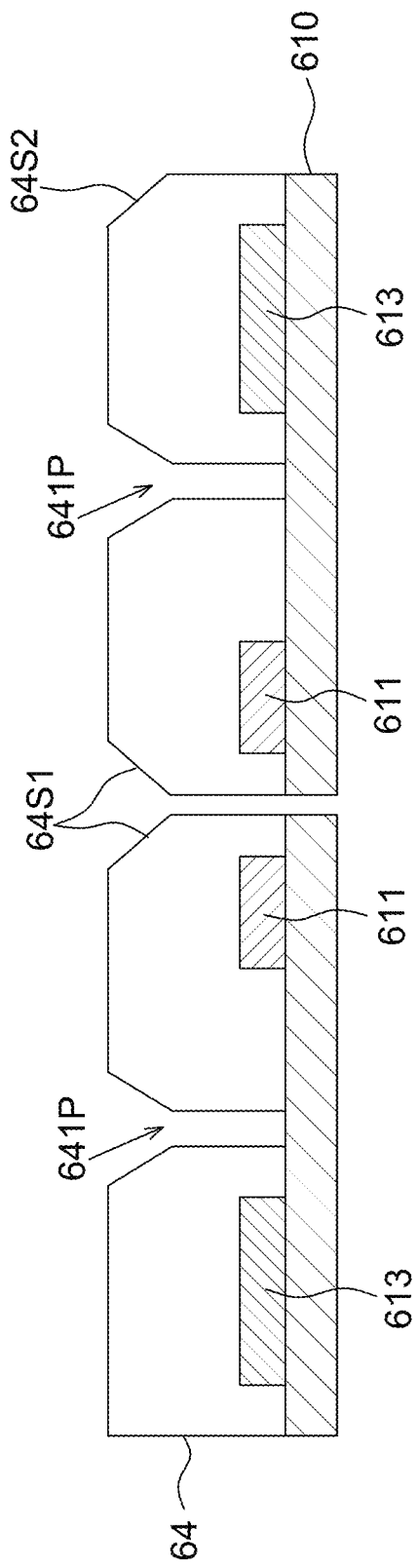

Please refer to FIGS. 6A to 6D, they are cross sectional views of manufacturing an optical machine 600 of a smoke detector according to a second embodiment of the present disclosure. Firstly, a substrate 610 is provided, and a light source 611 and a light sensor 613 are arranged on the substrate 610, as shown in FIG. 6A. It is possible to manufacture multiple (e.g., shown as two herein, but not limited to) optical machines 600 at the same time. Next, a transparent gel 64 is formed on the substrate 610 to encapsulate the light source 611, the light sensor 613 and a part of upper surface of the substrate 610, as shown in FIG. 6B. Next, cutting means in semiconductor packaging process (e.g., cutting blade) is used to cut a vertical trench 641P, a first tilted surface 64S1 and a second tilted surface 64S2, as shown in FIG. 6C. Next, the cutting blade is used to separate different optical machines 600, as shown in FIG. 6D. Finally, opaque material is filled in the vertical trench 641P to form the light blocking wall 641, and a metal coating layer (used as light blocking layer) is formed at the side (all or a part of side surface), the first tilted surface 64S1 and the second tilted surface 64S2 of the transparent gel 64 to accomplish the optical machine 600 according to the second embodiment of the present disclosure. The part of the surface of the transparent gel 64 unwilling to form the light blocking layer is firstly formed with a mask, which is then removed after the light blocking layer is accomplished. That is, the light blocking layer is formed by photolithography process.

Please refer to FIG. 7, in other aspects, the light blocking wall 643 is not formed by filling opaque material in the vertical trench 641P of the transparent gel 64 but formed by coating a metal layer on the surface of the vertical trench as the light blocking layer 741, e.g., formed using the same way as the first light blocking layer 643 and the second light blocking layer 645.

In another aspect, the first light blocking layer 643 extends into the transparent gel 64 to block a part of an emission angle of the light source 613 far away from the light sensor 613, e.g., using cutting means mentioned above. In other words, the metal coating layer for light blocking is formed on and/or inside the transparent gel 64 without particular limitations as long as the detected reference light intensity of the light sensor 613 is decreased.

In another aspect, the optical machine uses an external light source, i.e. not including a light source therein. For example referring to FIG. 6E, in this aspect the optical machine includes a right half part of the right optical machine in FIG. 6E. That is, the optical machine includes the substrate 610, the light sensor 613, the transparent gel 64 and the light blocking layer 645. The optical sensor 613 is arranged on the substrate 610. The transparent gel 64 encapsulates the light sensor 613 and a part of surface of the substrate 610, and has a tilted surface 64S2 extending from the side of the transparent gel 64 to above the light sensor 613. The light blocking layer 645 is formed on the side (all or a part) of the transparent gel 64 and the tilted surface 64S2 so as to block a part of an upper area of the light sensor 613. In this aspect, the light blocking layer 645 extends only to the tilted surface 64S2 or further to an upper surface of the transparent gel 64 depending on the required reference light intensity.

The above first and second embodiments can be combined to form another embodiment of the present disclosure.

As mentioned above, the conventional smoke detector has a larger size and a high false alarm rate due to the environmental change. Accordingly, the present disclosure further provides a smoke detector (e.g., FIGS. 3 to 5) that improves a ratio of light intensity variation with respect to reference light intensity by reducing the reference light intensity inside a cover. In addition, the present disclosure further provides a miniaturized optical machine (e.g., FIGS. 6E and 7) and a manufacturing method thereof (e.g., FIGS. 6A to 6E) that use a coating layer to replace a light blocking member of the smoke detector to reduce the size thereof.

Figure 8:
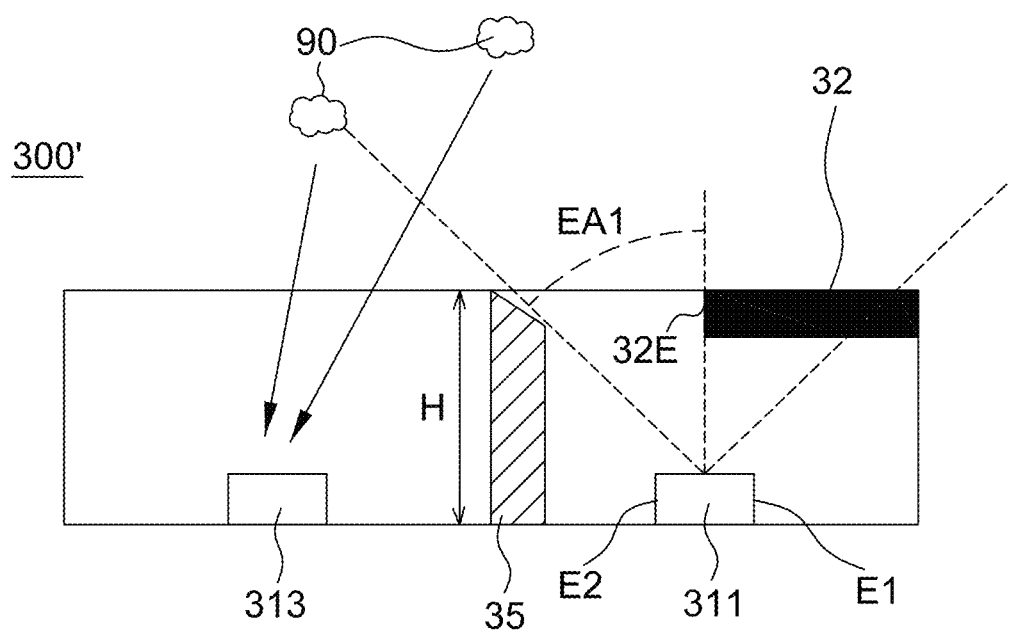
FIG. 8 is an operational schematic diagram of an optical machine of a smoke detector according to a third embodiment of the present disclosure.

Please refer to FIG. 8, it is an operational schematic diagram of an optical machine 300' of a smoke detector according to a third embodiment of the present disclosure. To further improve total intensity of scattered light from the smoke 90, a tilted top surface is arranged at a light blocking wall 35 between the first light source 311 and the light sensor 313. Accordingly, a range of the smoke 90 being illuminated by the first light source 311 is increased. The light blocking wall 35 is used to block light emitted by the first light source 311 to directly propagate to the light sensor 313.

In this embodiment, a height H of the light blocking wall 35 is preferably arranged between a half of an arranged height of the light blocking member 32 and the same height as the arranged height of the light blocking member 32. Meanwhile, an inclined angle of the top surface is determined, for example, according to the height H of the light blocking wall 35 as well as a transverse distance between the light blocking wall 35 and the first light source 311.

Furthermore, it is possible to combine the third embodiment to the first embodiment and/or the second embodiment to form an alternative embodiment.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. An optical machine of a smoke detector, the optical machine comprising:
a substrate;
a light sensor, arranged on the substrate;
a light source, arranged on the substrate and having an emission angle;
a transparent gel, encapsulating the light sensor and the light source, and having a first tilted surface extending from a first side of the transparent gel toward the light source to be connected to an upper surface of the transparent gel above the light source, wherein a part of a top surface of the light source is opposite to the first tilted surface in a longitudinal direction and another part of the top surface of the light source is opposite to the upper surface of the transparent gel in the longitudinal direction; and
a first light blocking layer, formed on the first side and the first tilted surface of the transparent gel to block a part of the emission angle of the light source and to expose the another part of the top surface of the light source in the longitudinal direction.

2. The optical machine as claimed in claim 1, wherein an angle of the first tilted surface relative to the upper surface is between 15 degrees and 80 degrees.

3. The optical machine as claimed in claim 1, wherein the first light blocking layer further extends from the first tilted surface to cover a part of the upper surface of the transparent gel above the light source.

4. The optical machine as claimed in claim 1, wherein the first light blocking layer is a metal coating layer.

5. An optical machine of a smoke detector, the optical machine comprising:
   a substrate;
   a light sensor, arranged on the substrate;
   a light source, arranged on the substrate and having an emission angle;
   a transparent gel, encapsulating the light sensor and the light source, and having a first tilted surface extending from a first side of the transparent gel toward the light source to be above the light source;
   a first light blocking layer, formed on the first side and the first tilted surface of the transparent gel to block a part of the emission angle of the light source; and
   a light blocking wall in the transparent gel between the light source and the light sensor, wherein
   the light blocking wall comprises opaque material filled in a vertical trench of the transparent gel, and the first tilted surface and the light blocking wall are arranged at two opposite sides of the light source.

6. The optical machine as claimed in claim 1, further comprising a light blocking wall in the transparent gel between the light source and the light sensor, wherein
   the light blocking wall comprises a metal layer coated on a vertical trench of the transparent gel, and
   a cross section of an upper part of the light blocking wall is larger than a cross section of a lower part of the light blocking wall.

7. The optical machine as claimed in claim 1, further comprising a second light blocking layer formed on a second side, opposite to the first side, of the transparent gel and on a part of the upper surface of the transparent gel above the light sensor.

8. The optical machine as claimed in claim 7, wherein the transparent gel further comprises a second tilted surface extending from the second side to above the light sensor, and the second light blocking layer is further formed on the second tilted surface.

9. The optical machine as claimed in claim 8, wherein the second tilted surface and the first tilted surface relative to the upper surface have different angles.

10. The optical machine as claimed in claim 1, wherein the first light blocking layer further extends to inside the transparent gel and blocks the part of the emission angle.

11. The optical machine as claimed in claim 5, wherein
    the first tilted surface of the transparent gel is connected to an upper surface of the transparent gel, and
    a part of a top surface of the light source is opposite to the first tilted surface in a longitudinal direction and another part of the top surface of the light source is opposite to the upper surface of the transparent gel in the longitudinal direction.

12. The optical machine as claimed in claim 5, wherein a cross section of an upper part of the light blocking wall is larger than a cross section of a lower part of the light blocking wall.

\* \* \* \* \*